(12) United States Patent
Sekine et al.

(10) Patent No.: US 7,943,382 B2
(45) Date of Patent: May 17, 2011

(54) METHOD FOR INSPECTING FAT-SOLUBLE VITAMIN AND/OR FAT-SOLUBLE FOOD FACTOR BY SALIVA ANALYSIS

(75) Inventors: Kyouichi Sekine, Tokyo (JP); Tatsuo Uetake, Tokyo (JP)

(73) Assignee: Mitsubishi Chemical Medience Corporation, Tokyo (JP)

( * ) Notice: Subject to any disclaimer, the term of this patent is extended or adjusted under 35 U.S.C. 154(b) by 1183 days.

(21) Appl. No.: 10/598,297

(22) PCT Filed: Mar. 3, 2005

(86) PCT No.: PCT/JP2005/003651
§ 371 (c)(1),
(2), (4) Date: Aug. 23, 2006

(87) PCT Pub. No.: WO2005/085843
PCT Pub. Date: Sep. 15, 2005

(65) Prior Publication Data
US 2007/0172550 A1 Jul. 26, 2007

(30) Foreign Application Priority Data

Mar. 3, 2004 (JP) .................. 2004-059834
Oct. 25, 2004 (JP) .................. 2004-309702

(51) Int. Cl.
*G01N 33/48* (2006.01)
*G01N 33/02* (2006.01)
(52) U.S. Cl. .............. 436/63; 436/20; 436/86; 436/161; 436/174; 436/178
(58) Field of Classification Search .................... 436/20, 436/63, 86, 161, 174, 177, 178; 426/72
See application file for complete search history.

(56) References Cited

U.S. PATENT DOCUMENTS
5,260,031 A * 11/1993 Seymour ..................... 422/101

FOREIGN PATENT DOCUMENTS
| JP | 5-203578 A | 8/1993 |
| JP | 2000-9727 A | 1/2000 |
| JP | 2002-168848 A | 6/2002 |

OTHER PUBLICATIONS

Sekine et al. BioFactors, vol. 25, 2005, pp. 205-211.*
Lumikari et al., "Saliva concentration of some Selected Proteins and Glycoprotein Markers in Man After Supplementary Intake of Beta-Carotene," International Journal of Vitamin and Nutrition Research, 58(2): 171-177 (1998).
Folkers et al., "Lovastatin decreases coenzyme Q levels in humans," Proc National Academy of Science USA, 87: 8931-8934 (1990).
Alam BS et al., "Effects of Excess Vitamin A and canthaxanthin on Salivary Gland Tumors," Nutr. Cancer, 11(4):233-241 (1998).
Katsukawa et al., "Effects of dietary ingredients on salivary composition," Medicine and Biology, 137(6):327-330 (1998).

* cited by examiner

*Primary Examiner* — Maureen M Wallenhorst
(74) *Attorney, Agent, or Firm* — Joseph H. Kim; JHK Law (57) ABSTRACT

For a method for inspecting in vivo migration of fat soluble vitamins and/or fat soluble food factors in the ingestion of a drug or a health supplement, it is necessary to use saliva as a specimen, to contact a saliva collecting tool with a certain amount of saliva to absorb for collection, and to select a solvent for efficiently extracting a measurement target component from the saliva collecting tool. Accordingly, there are provided a method for inspecting in vivo migration of fat soluble vitamins and/or fat soluble food factors in the ingestion of a drug or a health supplement, by using saliva as a specimen to determine; the property of a saliva collecting tool; and a method for extracting from the saliva collecting tool.

21 Claims, 6 Drawing Sheets

METHOD FOR INSPECTING FAT-SOLUBLE VITAMIN AND/OR FAT-SOLUBLE FOOD FACTOR BY SALIVA ANALYSIS

TECHNICAL FIELD

The present invention relates to a method for inspecting fat-soluble vitamins and/or fat-soluble food factors by saliva analysis

BACKGROUND OF THE INVENTION

Dietary Supplement, which is translated as "health supplement" or "nutritional supplement", is ingested mainly to supplement nutritional components such as vitamin, mineral, and amino acid which are apt to be scrimpy in everyday life (hereinafter, may be referred to "supplement", "health supplement" or "nutritional supplement"). In the U.S., there are laws about supplements, and supplements are positioned as a new genre different from both foods and pharmaceuticals, and have been approved to label with a Health Claim of the activity to reduce the risk of diseases.

Analysis of in vivo migration of an administered substance to a living body, which is usually executed by determining contents such as blood level and urine level, needs specimen collection executed by a specific facility such as a medical institution. Therefore it has been difficult to analyze in vivo migration of a nutritional component contained in a nutritional supplement or the like according to the convenience of a subject.

Saliva may also be a specimen but has inadequate to use as a specimen for a method for analyzing in vivo migration of a nutritional component contained in an ingested health supplement. It is partly because a method for collecting specimen has not been established to give a reproducible value.

Ubidecarenone (CoQ10), which is a nutritional component comprised in the nutritional supplements and constantly presents in mitochondrias, is a coenzyme involved in energy production in which ADP is converted to ATP by oxidation from a reduced form of ubidecarenol to an oxidized form of ubidecarenone (CoQ10) in the electron transport system. In a living body, CoQ10 is not present in the blood, but mainly in the tissues, and about 90% of CoQ10 is present as a reduced form in cell membranes and phospholipid double membranes in organelles. The CoQ10 can be synthesized through enzyme reactions in common with the cholesterol biosynthesis pathway in a human body, therefore its synthesis is supposed to be inhibited in a patient treated with a statin base drug although it is not a vitamin (Proc Natl Acad Sci. USA, 1990 November; 87: 8931-4, Lovastatin decreases coenzyme Q levels in humans, Folkers K, Langsjoen P, Willis R. Richardson P, Xia L J, Ye C Q, Tamagawa H.). A Statin base drug with higher lipophilicity is supposed to have higher degree of inhibitory potency against the synthesis, and ingestion of CoQ10 is considered to be useful for avoiding the adverse effects by the drug. Clinical trials by its combination therapy have been already performed in the U.S.

Tocopherol (vitamin E), which is a nutritional component comprised in the health supplements, is a major substance to prevent a lipid radical from oxidation, because tocopherol radicals collides with each others to eliminate the radical. A large abundance of tocopherol lowers incidence of collision among the radicals to cause the radical to remain longer. However, a reduced form of CoQ10 in vivo is believed to be potently associated with the tocopherol radicals to eliminate the radical.

Meanwhile, in the developed countries, the mortality rate in myocardial infarction and cerebral infarction potentially resulting from arteriosclerosis is being increased, and the number of diabetics potentially resulting from the lifestyle is rising, and in Japan, diabetes is tops in the novel pathogenesis resulting in hemodialysis patients.

These so-called life-style related diseases are considered to be strongly affected by dietary habit and strongly involve increased oxidative stress in vivo, therefore aggressive ingestion of a substance against oxidative stress is recommended as nutritional supplements. However, a so-called non-patient, who is not at a stage to visit a hospital, loses a chance to receive health management by a doctor to fall in a worsened symptom before visiting the hospital. This too late treatment may contribute to increased number of patients.

There has been no report about concentrations and contents of fat-soluble vitamins such as tocopherol or of fat-soluble food factors such as CoQ10 or lycopene found in saliva and salivary gland associated with salivation. It may be because saliva levels of a vitamin impossible to synthesize in a human body and a so-called supplement capable of being ingested by diet are easily assumed to be influenced by amount and sort of the foods and drinks left in the oral cavity, the existing substances derived from various bacteria and fungi, and additionally plaque bacteria flora on the surface of a tooth.

In addition, although fat-soluble β-carotene which is a provitamin of vitamin A has been known to show a positive correlation between the serum level and the whole saliva level (for example, refer to Nonpatent documents No. 1 and 2), the object of the reporters in Nonpatent documents No. 1 is "to confirm and verify assumption that an ingested β-carotene is useful for maintenance of oral hygiene by enhancing production and secretion of an antibacterial protein such as glycoprotein or lysozyme in the salivary gland", but not to assess levels of in vivo migration of β-carotene. The reporters in Nonpatent documents No. 1 report that β-carotene in the parotid saliva could not be detected. Thus it is significantly meaningful if it would get verified that β-carotene can be detected from saliva or even parotid saliva, and that saliva is a biological sample suitable for analyzing fat-soluble vitamins and/or fat-soluble food factors. Furthermore, it is particularly significant to provide a method for analyzing and inspecting fat-soluble vitamins and/or fat-soluble food factors in saliva.
Nonpatent document No. 1: Int. J. Vitam. Nutr. Res. 1988; 58(2): 171-7 Saliva concentrations of some selected proteins and glycoprotein markers in man after supplementary intake of beta-carotene. Lumikari M. Johansson I., Ericson T., Virtamo J.
Nonpatent document No. 2: Nutr. Cancer 1988; 11(4): 233-41 Effects of excess vitamin A and canthaxanthin On salivary gland tumors. Alam B S, Al am SQ, Weir J C Jr.

DISCLOSURE OF THE INVENTION

Problems to be Solved by the Invention

An object of the present invention is to provide a simple means of inspecting in vivo migration of fat-soluble vitamins and/or fat-soluble food factors which are nutritional components contained in health supplements, drugs or foods (hereinafter, may be referred to "health supplement or the like") in ingestion of health supplements or the like.

Means for Solving the Problem

The present inventors repeated keen study to solve the above problems, as a result, saliva was found to be available as a specimen for inspecting in vivo migration of fat-soluble vitamins and/or fat-soluble food factors which are nutritional components contained in health supplements or the like, in ingestion of health supplements or the like. Even if the concentration level of analytes in the saliva was approximately 1/10 of the blood level, it was found that assessment was certain. In particular, the present inventors found that β-carotene and other food factors such as lycopene, tocopherol and CoQ10 could be detected and analyzed in parotid saliva supposed to be undetectable as well as whole saliva. Also, the present inventors found that the concentration of CoQ10 or the like in parotid saliva has better positive correlation with the blood level than that in whole saliva, and diligently improved a method of collecting parotid saliva. Unfavorably, an absorber is used for saliva collection to adsorb fat-soluble vitamins and/or fat-soluble food factors in saliva regardless of its material. Therefore, the present inventors devised a collecting tool to allow contact with a certain volume of saliva and found that an extraction solvent which can well recover fat-soluble vitamins and/or fat-soluble food factors adsorbed to the collecting tool can be used to analyze correctly the concentration in saliva. The present invention is completed based on these findings.

Therefore, the present invention comprises:
1. A method for inspecting fat-soluble vitamins and/or fat-soluble food factors in vivo, comprising analyzing the fat-soluble vitamins and/or the fat-soluble food factors in saliva.
2. A method for inspecting in vivo migration of fat-soluble vitamins and/or fat-soluble food factors contained in ingested health supplements, drugs or foods, comprising analyzing fat-soluble vitamins and/or fat-soluble food factors in saliva.
3. The method according to previous aspect 2, wherein the inspecting is conducted on the basis of concentrations of the fat-soluble vitamins and/or the fat-soluble food factors in saliva of a subject before ingestion of the health supplements, drugs or foods, or the mean concentration of the fat-soluble vitamins and/or the fat-soluble food factors in saliva of a control group ingesting no health supplements, drugs or foods.
4. A method for inspecting effect or action of an administered therapeutic agent on biosynthesis and metabolism of fat-soluble vitamins and/or fat-soluble food factors, wherein the method is conducted by using fat-soluble vitamins and/or fat-soluble food factors in saliva as indicators.
5. The method according to previous aspect 4, wherein the inspecting is conducted on the basis of concentrations of the fat-soluble vitamins and/or the fat-soluble food factors in saliva of a subjects before taking the therapeutic agent, or the mean concentration of the fat-soluble vitamins and/or the fat-soluble food factors in saliva of a control group taking no therapeutic agent.
6. A method for assessing suitability of ingestion or an intake of health supplements, drugs or foods comprising fat-soluble vitamins and/or fat-soluble food factors, wherein the method uses a method according to previous aspect 2 or 3.
7. A method for assessing suitability of administration or a dosage of a therapeutic agent having effect or action on biosynthesis and metabolism of fat-soluble vitamins and/or fat-soluble food factors, wherein the method uses a method according to previous aspect 4 or 5.
8. The method according to any of previous aspects 1 to 7, wherein saliva is parotid saliva.
9. The method according to previous aspect 8, wherein parotid saliva is collected using a saliva collecting tool which collects parotid saliva selectively and quantitatively.
10. The method according to previous aspect 9, wherein the saliva collecting tool has (a) a collection part comprising an absorber for absorbing saliva irreversibly and (b) a quantification part for quantifying the amount of saliva collected to the absorber.
11. The method according to previous aspect 10, wherein the saliva collecting tool has further a storage container part for holding a saliva preservative solution in which the absorber with the absorbed saliva is dipped to preserve.
12. The method according to previous aspect 11, wherein the saliva preservative solution is a water-soluble organic solvent.
13. The method according to any of previous aspects 1 to 12, comprising:
   (a) a process for extracting the collected saliva, the absorber with the absorbed saliva, and/or the preservative solution with the preserved absorber with a water-soluble organic solvent, a hydrocarbon base organic solvent, or a mixture of isopropanol and ethyl acetate,
   (b) a process for using the extract as an analysis sample to separate the fat-soluble vitamins and/or the fat-soluble food factors by high-performance liquid chromatography, and
   (c) a process for detecting the separated fat-soluble vitamins and/or fat-soluble food factors.
14. The method according to any of previous aspects 1 to 13, wherein the fat-soluble vitamins and/or the fat-soluble food factors are at least one substance selected from a group consisting of CoQ10, lycopene, β-carotene and tocopherol.
15. A method for screening drugs or health supplements, wherein the method uses a method according to any of previous aspects 1 to 14.

Effects of the Invention

The methods provided by the present invention allow analysis of fat-soluble vitamins such as tocopherol and β-carotene and/or fat-soluble food factors such as lycopene and CoQ10 from saliva, and facilitate simple inspection in vivo migration of the fat-soluble vitamins and/or fat-soluble food factors which are nutritional components contained in health supplements or the like, in ingestion of the health supplements or the like. Namely, the methods in the present invention could confirm that the target fat-soluble vitamins and/or fat-soluble food factors in saliva increased with the intake of the health supplements or drugs. Consequently, saliva allows noninvasive evaluation of nutritional values of foods or the like, and assessment of degree of in vivo migration of fat-soluble vitamins and/or fat-soluble food factors by ingestion of health supplements or drugs, and noninvasive assessment of effect or action of an administered therapeutic agent on biosynthesis or metabolism of the fat-soluble vitamins and/or fat-soluble food factors. Therefore, the present invention is available for development of drugs, health supplements or the like. Furthermore, the methods of the present invention allow noninvasive assessment of suitability of ingestion of health supplements, drugs or foods comprising fat-soluble vitamins and/or fat-soluble food factors, or suitability of administration of a therapeutic agent having effect or action on biosynthesis or metabolism of fat-soluble vitamins and/or fat-soluble food factors.

BEST MODE FOR CARRYING OUT THE INVENTION

The present invention is explained below in details by the embodiments (representative examples), but not specified by those contents.

The essence of the present invention is based on a finding that saliva, a noninvasive collectable specimen, is useful for inspecting in vivo migration of fat-soluble vitamins and/or fat-soluble food factors contained in a health supplement or the like in ingestion of the health supplement or the like. In the present invention, conduct to measure and methods to measure are referred to analysis and analysis methods respectively, and values obtained by analysis of individual sample and a plurality of samples are referred to measured values.

In addition, for the fat-soluble vitamins and/or fat-soluble food factors used in the present invention, followings are exemplified. The fat-soluble vitamins include particularly tocopherol of vitamin E and β-carotene of provitamin A. The fat-soluble food factors include CoQ10 which can be synthesized in living bodies and lycopene which is an antioxidant, is not required to ingest because it is not a vitamin, but preferably is aggressively ingested to maintain and promote health. The specimen is sampled saliva, in particular preferably parotid saliva. This parotid saliva is sampled under a more selected environment to give a more correct value. Approximately 70% of saliva is secreted from the sublingual gland and the submandibular gland, and another approximately 30% is secreted from the parotid gland. The object of the present invention can be achieved by sampling this parotid saliva more selectively. For this sampling, a saliva collecting tool already marketed (e.g. Saliva-sampler (Saliva Diagnostic Systems Inc.), Orasure (Orasure Technologies, Inc., Translated National Publication of Patent Application No. Hei 5-506925), Salivet (Assist Co., Ltd.)) can be used, and the tool has preferably a shape that at least allows more selective contact with the exit site of parotid saliva in the oral cavity. For example, the flattened sampling part is more preferable for collecting saliva. Parotid saliva is collected by inserting an absorber between the teeth and the inside of the cheek, for example. The amount of collected saliva depends on types of the absorber of the collecting tool, and it is indispensable for obtaining relative values that a specific absorber is used, and a certain amount of saliva is brought contact with a certain amount of the absorber which adsorbs fat-soluble vitamins and/or fat-soluble food factors. That means, it is necessary that the collector takes care to keep the ratio of the amounts of the absorber and the contacting saliva and regulates the amount of the used absorber so that a solvent may be added to recover the analysis sample as a liquid. Concretely, the absorber is preferably used with irreversibly absorbed saliva, and includes an absorber using capillary phenomenon.

The collecting tool may be supplied with a function like a collecting indicator to keep a constant collection amount. This indicates, for example, that the amount of the collected saliva may be confirmed by any means such as capillary phenomenon. For the absorber, any material is usable as far as it absorbs water and is insoluble in alcohols like ethanol. An artificial polymer material such as polyester-fiber or urethane foam and a natural material such as absorbent cotton, paper or pulp, can be used, and a cotton material is most suitable. Additionally, the collecting tool may be supplied with a storage container part for preserving the absorber with absorbed saliva. Furthermore the storage container part may hold a saliva preservative solution to dip and preserve the absorber. The preservative solution may be any water-soluble organic solvent. Lower alcohols such as ethanol, methanol or isopropanol are exemplified. For an analysis laboratory to take the collecting tool with collected saliva from a subject by mail, the tool holds desirably ethanol in a concentration so as to be excluded from a combustible material or a poisonous material according to the postal regulation or the like. Also, the collecting tool may be any possible posting form, but is desirably a form which can be sent in a standard-size. The parotid saliva specimen, which is little affected by a physiological condition, is preferably collected between meals under a stable condition of saliva secretion, in particular desirably two hours or longer after meal, rather than immediately after meal under a condition of enhanced saliva secretion.

Collected saliva remaining in the collecting tool is preserved in the storage container and sent to an analysis laboratory or the like for analysis. In order to analyze the fat-soluble vitamins and/or fat-soluble food factors as target substances, the fat-soluble vitamins and/or fat-soluble food factors are just extracted and separated from the collecting tool, detected and quantified. Specifically, the method comprises: (a) a process for solvent-processing the collected saliva, the absorber with absorbed saliva and/or the preservative solution with the preserved absorber to extract the fat-soluble vitamins and/or the fat-soluble food factors, (b) a process for separating the fat-soluble vitamins and/or the fat-soluble food factors from the extract by high-performance liquid chromatography (HPLC) or the like, and (c) a process for detecting and quantifying the separated fat-soluble vitamins and/or the fat-soluble food factors by a known analysis method suitable for microassay, for example, using a UV detector or an electrochemical detector (ECD).

The preferable solvent is a solvent which can remove a protein and extract the target fat-soluble vitamins and/or fat-soluble food factors from the collected saliva, the absorber with the absorbed saliva and/or the preservative solution with the preserved absorber. For the fat-soluble vitamins and/or the fat-soluble food factors which are slightly water-soluble such as CoQ10 and tocopherol, the above-mentioned water-soluble solvent is more preferable, and a water-soluble solvent having a concentration suitable for extraction, specifically, ethanol having a final concentration of at least 75%, is most suitable. The other solvent includes methanol and isopropanol available for the ECD detector which is more sensitive than the UV detector. Additionally, for the fat-soluble vitamins and/or the fat-soluble food factors, including lycopene or β-carotene, which are extremely hard to dissolve in water or a mixture of ethanol and water, a hydrocarbon, a mixture of an ethyl acetate and isopropanol, or isopropanol can be used to extract well.

In order to extract, an absorber with 1 ml of saliva absorbed is supplied with a volume three times or more (approximately 66% or more) of ethanol as a solvent to contact. isopropanol and methanol having a volume five times or more relative to saliva should be contacted. The fat-soluble vitamin and/or the fat-soluble food factors are promptly extracted from the absorber, and they are not adsorbed again even after a long time. Absorbent cotton is suitably used by approximately 250 mg relative to 1 ml of saliva. The extracted specimen is analyzed, unprocessed or preprocessed by centrifugation for removing an agglomerated protein to recover the supernatant.

Numerical values (concentrations) in saliva, which are obtained by these analyses from subjects who ingest health supplements or the like comprising fat-soluble vitamins and/or fat-soluble food factors, indicate in vivo migration of the fat-soluble vitamins and/or the fat-soluble food factors contained in the ingested health supplements, drugs or foods. For example, these values are compared with the values in saliva from the subjects before ingestion of the health supplements, drugs or foods, or the mean value in saliva from a control group without ingestion of the health supplements, drugs or foods, allowing inspecting in vivo migration of the fat-soluble vitamins and/or the fat-soluble food factors, thereby assessing the health situation, absorbability, nutritional ability or the like in the subjects. A method for assessing suitability of ingestion or the intake of the health supplements, drugs or foods, is also provided.

Furthermore, numerical values in saliva, which are obtained by these analyses from subjects dosed with a therapeutic agent having effect or action on biosynthesis and metabolism of fat-soluble vitamins and/or fat-soluble food factors, can be used as an indicator of effector action of the therapeutic agent. For example, these values may be used to compare with the values in saliva of the subjects before administration of the therapeutic agent, or the mean value in saliva of a control group without administration of the therapeutic agent. A method for assessing suitability of administration or the dosage of the therapeutic agent is also provided. For example, as a therapeutic agent with effect or action on biosynthesis or metabolism of CoQ10, a statin base agent such as Mevalotin (Sankyo Co., Ltd.) or Lipitor (Pfizer Inc.) is known, and the CoQ10 level in saliva of a subject dosed with the therapeutic agent can be used as an indicator of the effect or action of the therapeutic agent.

Furthermore, these analysis methods allow tracing in vivo migration of the ingested fat-soluble vitamins and/or fat-soluble food factors and are available as methods for drug discovery or screening of novel health supplements.

For assessment based on the mean value (concentration) of the fat-soluble vitamins and/or the fat-soluble food factors in saliva of the control group, by way of example, a standard deviation of the mean value in the control group can be used. For example, a CoQ10 level in saliva of a subject ingesting CoQ10, which is far over the mean value +2SD for the control group, can be used as an indicator for directing the subject to reduce the intake, while the value, which is between the mean value −2SD and the mean value +2SD, can be used as an indicator for directing to increase the intake. In addition, saliva may be repeatedly collected at the later dates to inspect the CoQ10 level.

EXAMPLES

Hereinafter, the present invention will be described with examples. In the following examples, as representative examples of nutritional components contained in health supplements or the like, CoQ10 and tocopherol are used to confirm the effect, but the present invention is available for fat-soluble vitamins and/or fat-soluble food factors, and scope of the invention is not limited to these examples. In examples, CoQ10, tocopherol, lycopene and β-carotene were analyzed as follows.

(Analytical Condition)

HPLC was conducted in reference to a known method of an analysis method of CoQ10 in plasma (Analytical Biochemistry Vol. 250, p 66-73, 1997), and improved so as to be suitable for saliva analysis.

Pretreatment and Loading to an Autosampler

In pretreatment of the specimens, 20 µl of plasma and 180 µl of ethanol (Wako Pure Chemical Industries, Ltd.: HPLC grade) were added to an autosampler vial (sampler vial PP 250 µl: Shiseido Co., Ltd.) to have a final ethanol concentration of 90% (V/V), which was centrifuged under cooling by 1000 G for 5 minutes to precipitate proteins. In the case of directly collected saliva, 150 µl of ethanol was added to 50 µl of the specimen to have a final ethanol concentration of 75% (V/V), which was centrifuged under cooling by 1000 G for 5 minutes to precipitate proteins. In the case of parotid saliva collected using the Saliva-sampler, as the sampler adsorbs 1 ml of saliva as a fluid volume, 3 ml of ethanol (HPLC grade) was added to the sampler, and mixed by flipping upside down for 15 minutes, subsequently 200 µl was fractionated to each autosampler vial (sampler vial PP 250 µl: Shiseido Co., Ltd.), and centrifuged under cooling by 1000 G for 5 minutes to precipitate proteins. The centrifuged autosampler vial was loaded into the autosampler and subjected to HPLC.

(Column in Use)

The following three columns were prepared for HPLC.
1. Concentrator column: CAPCELL PAKC18 AQ 5 µm φ 2.0×35 mm (Shiseido Co., Ltd.)
2. Separation column: CAPCELL PAKC18 AQ 3 µm φ 2.0× 150 mm (Shiseido Co., Ltd.)
3. Reduction column: SHISEIDO CQ ID 2.0 mm×20 mm (Shiseido Co., Ltd.)

The concentrator column is used for concentrating the analysis target components in the sample and for removing hydrophilic foreign substances. The Separation column is used for purifying, refining, and detecting each component as a single component. The reduction column is used for reducing ubidecarenone (CoQ10) to ubidecarenol. Although reduction is useful especially for simultaneous analysis of CoQ10 together with fat-soluble vitamins and/or the fat-soluble food factors with OH groups such as tocopherol, lycopene or β-carotene, it is not particularly necessary in detection using a UV detector.

In case of no simultaneous analysis required, for example, for analysis of only CoQ10 in saliva, CAPCELL PAKC8 DD S-5φ 4.0×10 mm (Shiseido Co., Ltd.) as a concentrator column, and CAPCELL PAK AQ 3 μm φ 2.0×100 mm (Shiseido Co., Ltd.) as a separation column, are used, allowing better detection and quantification.

(Mobile Phase)

The followings were prepared as a developing solvent for the column.

Mobile phase 1: 6.122 g of an anhydrous sodium perchlorate is mixed to dissolve in 950 ml of methanol and 50 ml of distilled water, and then deaerated under vacuum with ultrasound.

Mobile phase 2: 6.122 g of an anhydrous sodium perchlorate is mixed to dissolve in 950 ml of methanol and 50 ml of isopropanol, and then deaerated under vacuum with ultrasound.

Mobile phase 1 is used for sending the infused sample to the concentrator column to keep the analysis target component in the column, removing hydrophilic foreign components such as proteins, polypeptides, amino acids, organic acids, saccharides and salts which could not completely removed from the analysis sample by a pretreatment, and effectively rinsing away hydrophobic non-analysis target components such as cholesterols, fatty acids, phospholipids and neutral fats contained in the biological sample in a large quantity. Mobile phase 2 is used for passing the liquid through the separation column from the time of infusion to completion of removal process of foreign components in the concentrator column, and on completing the removal process, then column-switching to flow reversely to the concentrator column, thereby to elute promptly the analysis target component and simultaneously sending the analysis target component to the separation column to purify, refine, and fractionate as a single component.

In preparation of mobile phase 1, it should be noted that the mixture ratio of distilled water to methanol is increased to cause difficulty to remove the hydrophobic foreign components, and that the mixture ratio is decreased to cause difficulty to remove the hydrophilic foreign components. In mobile phase 2, even if the mixture ratio of isopropanol to methanol is increased from 95:5 to 90:10 or 80:20, it does not bring a significant influence on elution from the concentrator column and separation of the components in the separation column. The anhydrous sodium perchlorate is added by 6.122 g to prepare a concentration of 50 mM, and it may be by 6 g or 7 g. The sodium perchlorate may not be an anhydride but be a hydrate. However, the reagent for preparing the mobile phase should be selected to use that of a maker and a lot so as to increase no noise of chromatogram, because the fat-soluble vitamins and/or the fat-soluble food factors is low in concentration in saliva than in blood. Or, it is better to add a small amount of an organic acid such as sodium formate and sodium acetate to the mobile phase. The amount of the added organic acid to mobile phases 1 and 2 is 1-10 mM, preferably 3-7 mM, more preferably 5 mM, allowing a wide range of problem-free measurement from the low-concentration side to the high-concentration side in the calibration curve.

(Separation Method)

Figure 1:
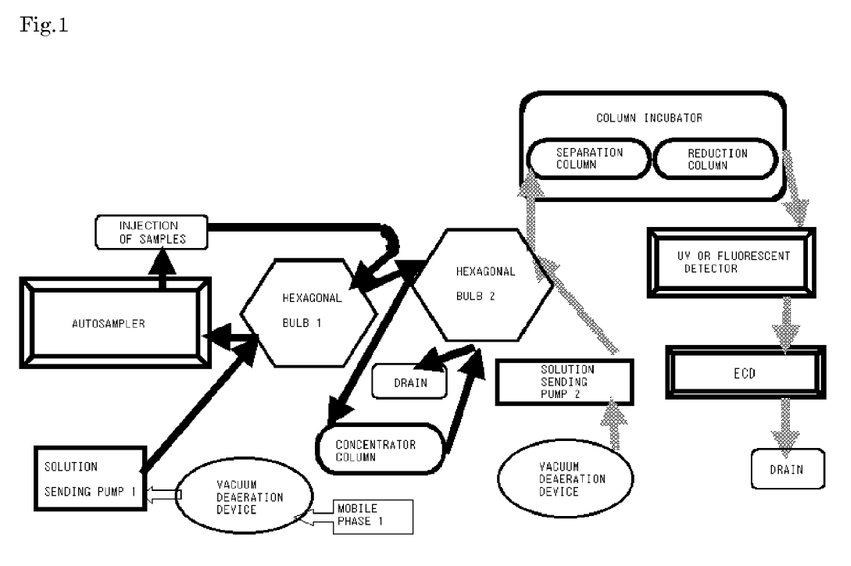
FIG. 1 shows a relation of interconnection among a separation system-constituting device, a mobile phase and columns from infusion of a sample to the time of concentration.
Figure 2:
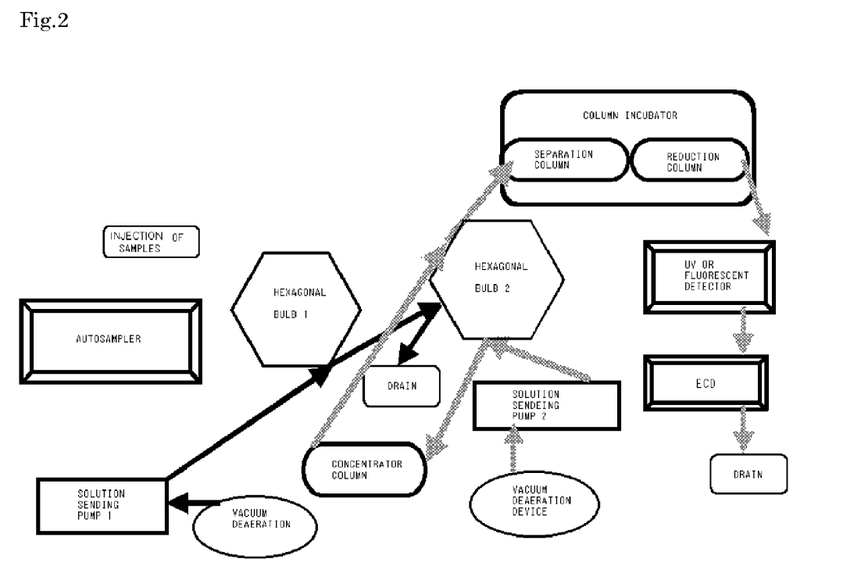
FIG. 2 shows a relation of interconnection among a separation system-constituting device, a mobile phase and columns from the time of elution through a concentrator column to the time of separation and refinement.

The separation method consists of a concentration process shown in FIG. 1 and a separation and quantification process shown in FIG. 2. The relation of interconnection among the separation system-constituting device, the mobile phase and the columns from infusion of sample to the time of concentration is shown in FIG. 1. The relation of interconnection among the separation system-constituting device, the mobile phase and the columns from the time of infusion through the concentrator column to the time of separation and formation is shown in FIG. 2. In FIGS. 1 and 2, flow of the mobile phase 1 is represented by black arrows, and flow of the mobile phase 2 is represented by gray arrows. The order of connection of the reduction column and separation column may be reversed according to an object. For example, for measuring CoQ10 in saliva, it doesn't matter whether it is the reduction column/separation column order, or the separation column/reduction column order. In the case of a sample which has a short retention period and includes many impurities, ubidecarenol, which is hardly detected in the collected saliva, is separated as CoQ10 with a long retention period, and then reduced to ubidecarenol to detect, resulting in good separation in peak. The sample and the reference standard are infused using an autosampler (trade name: HTS autosampler, Shiseido Co., Ltd.). Switching of passage is programmed using a system controller (trade name: EZChrom, Shiseido Co., Ltd.) which can automatically separate and analyze. For solution sending in the mobile phases 1 and 2, a total of two pumps, pump 1 and pump 2 respectively (trade name: Pump 3001, Shiseido Co., Ltd.), are used. The flow rates are 200 μl/min. for the mobile phase 1, and 400 μl/min. for the mobile phase 2 from the start of analysis to the end. During analysis, a mobile phase, which is previously passed through a three pathway-type vacuum deaeration device (trade name: SSC3215, Senshu Kagaku Co. Ltd.), is passed to cause no bubbles in the mobile phases 1 and 2. Furthermore, the reduction column and the separation column are tandemly connected and maintained at a constant temperature of 40° C. in a column oven (trade name: Type 3004, Shiseido Co., Ltd.). For hexagonal bulbs 1 and 2, a rinse bulb (trade name: Type 3034, Shiseido Co., Ltd.), and a high-voltage switching hexagonal bulb (trade name: Type 3011, Shiseido Co., Ltd.) are used respectively. For the autosampler, HTS autosampler (Shiseido Co., Ltd.) is used, and for control management of programming the whole system and process of numerical values, EZChrom (Shiseido Co., Ltd.) is used.

(Detection Method)

Figure 3:
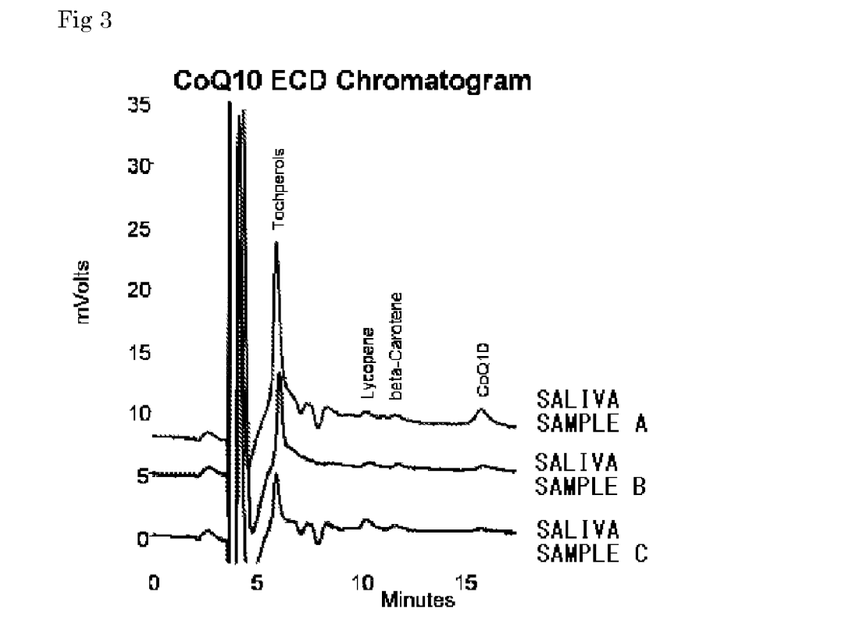
FIG. 3 shows chromatograms of the samples of a supplement-ingesting volunteer (saliva A), a non-ingesting volunteer (saliva B) and a person who drinks tomato juice regularly (saliva C).
Figure 4:
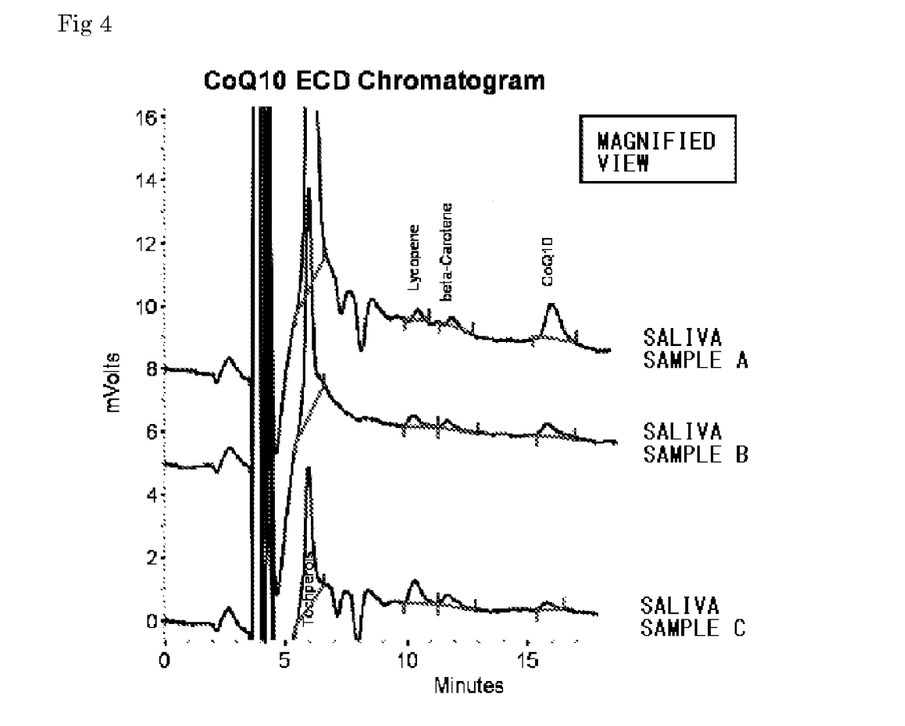
FIG. 4 shows a magnified view of peaks of lycopene and β-carotene by enlarging FIG. 3.

Ubidecarenol, tocopherol, lycopene and β-carotene can be quantitatively analyzed at 600 mV. CoQ10 with a carbonyl group, and tocopherol, lycopene and β-carotene with OH groups coexist in saliva. Therefore, CoQ10 is converted into ubidecarenol by reducing the carbonyl group to the OH group using the above-mentioned commercial online reduction column, and then detected in an oxidation mode using the amperometry-type electrochemical detector 3005 (Shiseido Co., Ltd.) or the pulse-type electrochemical detector 3016 (Shiseido Co., Ltd.) under the HPLC condition shown in FIGS. 1 and 2, allowing the bulk detection as shown in FIGS. 3 and 4.

The ECD detector was used after Sensitivity was set to 0.1 and Time Constant to a standard (Std.), and a maintained baseline level of approximately 1 nA was confirmed for every analysis. UV detectors or fluorescent detectors are useful for analysis of a tocopherol-rich sample. For the detection wavelength to set, a known wavelength is sufficient. For connecting an ECD detector and a UV or fluorescent detector to analyze quantitatively, the ECD detector is connected immediately before drain shown in FIGS. 1 and 2 so that a change in back-pressure behind the ECD detector may be decreased. Thereby, the noises of ECD detection signals can be reduced, allowing high-sensitive quantitative analysis.

(Calibration Curve, Sensitivity and Infusion Volume of the Sample)

When the amperometry-type electrochemical detector 3005 (Shiseido Co., Ltd.) or the pulse-type electrochemical detector 3016 (Shiseido Co., Ltd.) was used, 20 μl of reference standard mixtures of CoQ10, α-tocopherol, ubidecarenol, lycopene and β-carotene which were prepared to have their respective concentrations of 1.56 to 200 ng/ml, were infused to make a calibration curve capable of linear regression. When the HTS autosampler (Shiseido Co., Ltd.) is used as an autosampler, the infusion volume of a sample is normally 20 µl, but a concentrated sample is infused by 2 µl, and a diluted sample is infused by 150 µl to separate and quantify. The concentration rate of a pretreated sample can be raised and the infusion volume of a sample can be increased to change sensitivity to a desirable level.

Example 1

Chromatograms of the samples of the parotid saliva specimens A, B and C are shown in FIG. 3, and a magnified view of FIG. 3 is shown in FIG. 4 so that the peaks of lycopene, β-carotene and CoQ10 are easily visible. Parotid saliva was collected from a volunteer who was taking one CoQ Livlon tablet (trade name, Nissin pharma Inc., hereinafter may be referred to "Supplement N"), a commercial CoQ10 supplement, at 7:00 every morning and evening for a month, and then 1 ml of the saliva was supplied with 3 ml of ethanol for removing proteins to prepare a supernatant, 50 µl of which was infused to obtain the chromatogram of the sample of the parotid saliva specimen A. Meanwhile, the fat-soluble vitamins and the fat-soluble food factors were contained at 30 mg/tablet as for CoQ10, and 10 mg/tablet as for α-tocopherol in the Supplement N. The intakes from the supplement per day are 60 mg as for CoQ10, and 20 mg as for x-tocopherol. On the other hand, 1 ml of parotid saliva from a volunteer who took no commercial supplement was supplied with 3 ml of ethanol for removing proteins to prepare a supernatant, 50 µl of which was infused to obtain the chromatogram of the sample of the parotid saliva specimen B. Furthermore, parotid saliva was collected from a volunteer who was taking one commercial tomato juice can (180 ml) everyday and took a specified bland (trade name: Fully-Ripened Tomato, salt-free, ITO EN, LTD.) for a week, and then 1 ml of the parotid saliva was supplied with 3 ml of ethanol for removing proteins to prepare a supernatant, 50 µl of which was infused to obtain the chromatogram of the sample of the saliva C. The label showed that one can contained lycopene 20 mg and β-carotene 1.8 mg.

Comparing the peaks of tocopherol and CoQ10 in the chromatogram of the samples of parotid saliva A and B in FIG. 1, the A in a volunteer who was taking supplements shows a higher peak than the B. Additionally, comparing the chromatograms of the samples of parotid saliva B and C in FIG. 2, the peaks of lycopene and β-carotene in the person who drinks tomato juice regularly are obviously higher. Consequently, a volunteer with a higher intake showed a higher concentration in parotid saliva, and hence analysis of fat-soluble vitamins and/or fat-soluble food factors in saliva is useful for assessment of degree of in vivo migration of fat-soluble vitamins and/or fat-soluble food factors contained in ingested health supplements or the like.

Example 2

Ingestion Test of CoQ10 Part 1

11 volunteers were made to ingest orally two tablets (CoQ10 content: 100 mg in two tablets) of Q10AA Multi (trade name, Shiseido Co., Ltd., hereinafter may be referred to "Supplement S"), a commercial CoQ10 supplement, at 7:00 every morning continuously for a week. Meanwhile, the contents of the fat-soluble vitamins and fat-soluble food factors in the Supplement S are 50 mg/tablet as for CoQ10, and 16.4 mg/tablet as for α-tocopherol. Then parotid saliva, directly collected saliva and heparinized plasma were collected from PM 4:00 to 5:00, three times, before and one week after ingestion and two weeks after discontinuation of ingestion. The volunteer had the mouth rinsed with water, and kept quiet on a chair for 5 minutes, while the volunteer accumulated saliva in the oral cavity and discharge to initialize the oral cavity, followed by collecting saliva. Approximately 1 ml of saliva accumulated in the oral cavity was collected as directly collected saliva. In order to collect saliva from the parotid gland, an absorbent cotton of 2 g was put beneath the tongue to prevent contamination with saliva from sublingual gland and submandibular gland, while the Saliva-sampler comprising a cotton saliva absorber and an indicator which informed termination of collection by color change was inserted between the teeth and the cheek near the open of the parotid gland. The volunteer sat quiet on a chair, during which saliva was collected. For the 11 volunteers, the mean amount of saliva collected using the Saliva-sampler was 1 ml, and the fluctuation range was 0.9-1.1 ml with good reproducibility. In analysis of CoQ10 in saliva collected from the parotid gland, the Saliva-sampler with absorbed saliva was transferred to the peculiar tube, to which 3 ml of ethanol was added to have a final concentration of 75%. The resultant solution was mixed by flipping upside down for 10 minutes to extract from the absorber and coagulate proteins, and then centrifuged by 1000 G at 4° C. to remove fragments of the absorber and the unnecessary proteins to get a supernatant, 20 µl of which was subjected HPLC. Meanwhile, 2 g of absorbent cotton put beneath the tongue is not necessary for collecting of parotid saliva, and contamination of saliva from the sublingual gland and the submandibular gland can be avoided by swallowing as shown in Example 3. In pretreatment of directly collected saliva, 250 µl of the specimen was supplied with 750 µl of ethanol to mix, and centrifuged at 4° C. by 1000 G for 5 minutes for removing proteins to get a supernatant, 20 µl of which was subjected to HPLC. In pretreatment of plasma, 20 µl of the plasma was supplied with 180 µl of ethanol to mix, and then centrifuged at 4° C. by 1000 G for removing unnecessary proteins to get a supernatant, 20 µl of which was subjected to HPLC.

Example 3

Ingestion Test of CoQ10 Part 2

For the ingestion test of CoQ10, commercial supplement S containing CoQ10 of 50 mg per one tablet and commercial supplement N containing 30 mg per one tablet were used. 10 volunteers in the group S and 10 volunteers in the group N were made to ingest orally the supplement s and the supplement N respectively. For ingestion of supplement S, each volunteer was made to ingest orally two tablets at 9:00 every morning continuously for a week, and for the next week, made to ingest orally double amount, four tablets at 9:00 every morning continuously, and then stopped from ingestion for two weeks. For ingestion of supplement N, each volunteer was made to ingest orally three tablets at 9:00 every morning continuously for a week, and for the next week, made to ingest orally double amount, six tablets at 9:00 every morning continuously, and then stopped from ingestion for two weeks. As specimens in both the groups S and N, parotid saliva and heparinized plasma were collected from PM 4:00 to 5:00, total four times, that is, before and one week after ingestion, at double dose ingestion, and two weeks after discontinuation of ingestion. The volunteer had the mouth rinsed with water prior to collection, kept quiet on a chair for 5 minutes, while the volunteer accumulated saliva in the oral cavity and discharged to initialize the oral cavity, followed by collecting parotid saliva. For collection of parotid saliva, the Saliva-sampler is inserted between the teeth and the cheek near the open of the parotid gland, the volunteer sat quiet on a chair, during which saliva was collected, while the volunteer swallowed saliva, which was secreted from the sublingual gland and the submandibular gland and accumulated in the mandible, to prevent contamination with the saliva from the sublingual gland and the submandibular gland. For analysis of CoQ10 in saliva collected from the parotid gland, the Saliva-sampler with absorbed saliva was transferred to the peculiar tube holding 1 ml of 50% ethanol, to which 4 ml of ethanol was added to have a final concentration of 75%. The resultant solution was mixed by flipping upside down for 10 minutes to extract from the absorber and coagulate proteins, and then centrifuged at 4° C. by 1000 G for removing fragments of the absorber and unnecessary proteins to get a supernatant, 150 ml of which was subjected to HPLC. For pretreatment of plasma, 20 µl of plasma was supplied with 180 µl of ethanol to mix, and then centrifuged at 4° C. by 1000 G for removing unnecessary proteins to get a supernatant, 20 µl of which was subjected to HPLC. Meanwhile, the total number of specimens of saliva and plasma respectively was 79, because specimens of one volunteer in group N at the time of discontinuation of ingestion for two weeks (N4) could not be collected.

(Experiment of the Correlation Between the Blood Level and the Content in Saliva)

Figure 5:
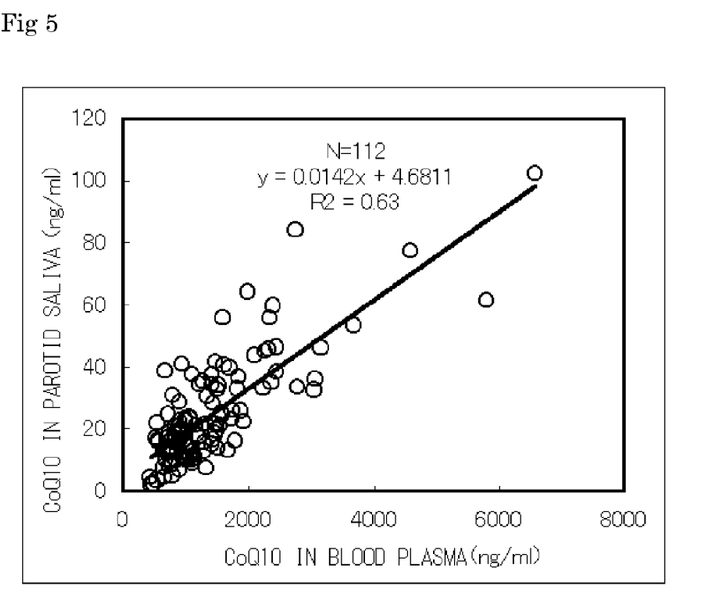
FIG. 5 shows correlation between the measured values of the CoQ10 in plasma and parotid saliva.
Figure 6:
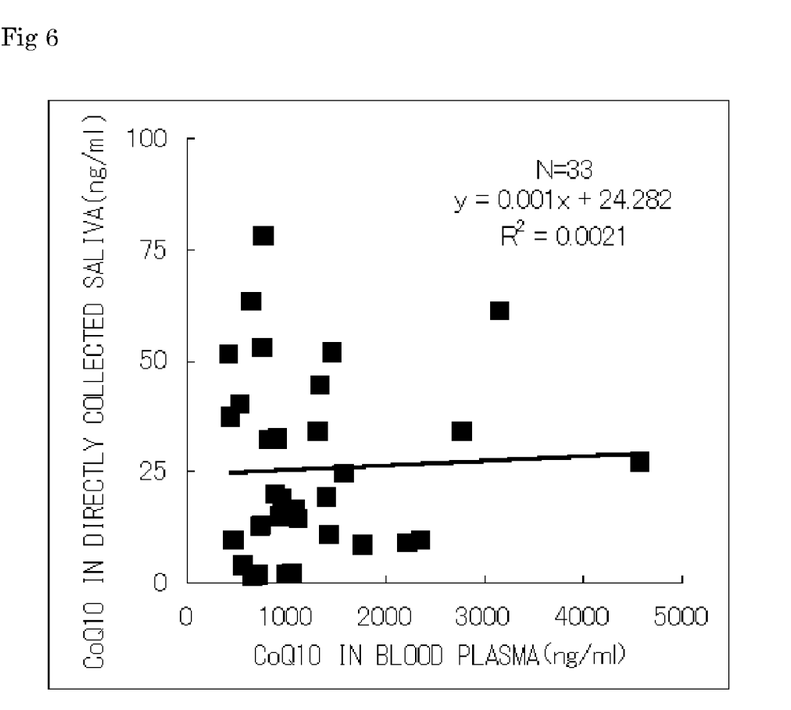
FIG. 6 shows correlation between the measured values of the CoQ10 in plasma and directly collected saliva.

As shown in FIG. 5, a good correlation was confirmed between the concentrations of CoQ10 in parotid saliva and plasma (hereinafter, the measured concentration of CoQ10 will be referred to "CoQ10 level") of the 112 specimens obtained in examples 2 and 3. As shown in FIG. 6, there was a weak but recognizable correlation between the CoQ10 levels in directly collected saliva and plasma. Thereby, it was confirmed that analysis of the values in saliva, particularly parotid saliva could correctly assess the amount of in vivo migration of nutritional supplements or the like.

Example 5

Transition of the CoQ10 Level in Parotid Saliva Depending on Ingestion States of Supplements with CoQ10

Figure 7:
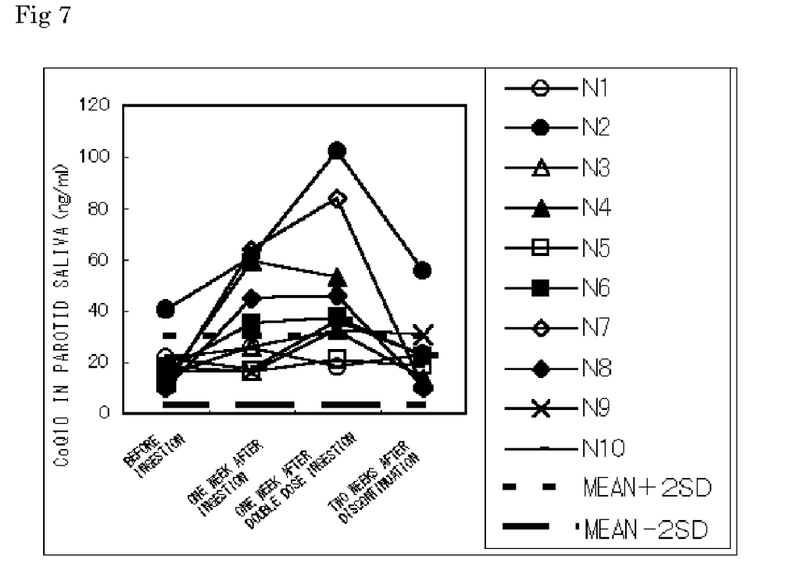
FIG. 7 shows transition of the CoQ10 level in parotid saliva depending on the statuses of ingestion of a CoQ10-containing supplement.

The ingestion states of Supplement N in example 4, that is, before ingestion, one week after ingestion, one week after double dose ingestion, and two weeks after discontinuation of ingestion, were arranged on the horizontal axis, and the CoQ10 levels in parotid saliva were arranged on the vertical axis, and transition of the CoQ10 level in parotid saliva depending on ingestion states of supplements with CoQ10 was shown in FIG. 7. In general, CoQ10 ingested after meals is likely to migrate in vivo more smoothly, and for efficient ingestion, it is supposed to be better ingested within 30 minutes after meals. The volunteer N1 in FIG. 7 had customarily taken no breakfast every morning in recent years, also the volunteer N5 had customarily often lacked breakfast, and therefore they could not be expected to show efficient in vivo migration in spite of ingestion of the CoQ10 supplement. The CoQ10 levels in parotid saliva of the N1 and N5 were hardly increased in spite of the increased amount of the supplement, and a reasonable behavior was observed. The volunteer N9 had regularly taken breakfast at about AM 6:00 every morning but ingested the supplement at AM 9:00, approximately three hours after breakfast, which might result in inefficient ingestion and small increase of the CoQ10 level in parotid saliva in spite of supplement ingestion. Other 7 volunteers showed facts that the CoQ10 levels in parotid saliva were increased by ingestion of the supplement with CoQ10, furthermore increased by more ingestion, and decreased after discontinuation of ingestion, indicating that the ingestion states reflected the transition. As a result, these suggest that inspection of the CoQ10 level in parotid saliva is useful as a criterion of suitable ingestion of the CoQ10 supplement.

Example 6

Application of the Mean Level and SD of CoQ10 in Parotid Saliva of Non-Supplement-Ingesting Volunteers as a Standard for Individually Setting the Intake It is known that even if volunteers ingest a CoQ10 supplement within 30 minutes after meals, which is supposed to be suitable for efficient absorption, they shows different increased blood levels in spite of the same products and the same amount because of wide individual variability in absorption. Therefore, a standard that can assess an individually suitable intake is required. It can be easily understood from FIG. 7 that the mean level and SD (standard deviation) of CoQ10 in parotid saliva of non-CoQ10 supplement-ingesting volunteers is useful as an example of the standard. A case that a volunteer, who is taking the CoQ10 supplement at an adequate time after meals, ingests it to increase the blood level up to a limit of the CoQ10 level of a non-ingesting volunteer, will be taken as an example for explanation. If a CoQ10 level in parotid saliva is far over the mean value +2SD, the intake is reduced, and if it is between the mean value −2SD and the mean value +2SD, the intake is increased, and the CoQ10 level is repeated inspected in saliva collected again at later dates, allowing the object to be achieved. In addition, the mean level and 2SD in FIG. 7 are obtained from the CoQ10 levels in parotid saliva of the 55 non-CoQ10 supplement-ingesting volunteers, the mean level is 17.0 ng/ml and the 2SD is 13.5 ng/ml.

Example 7

Figure 8:
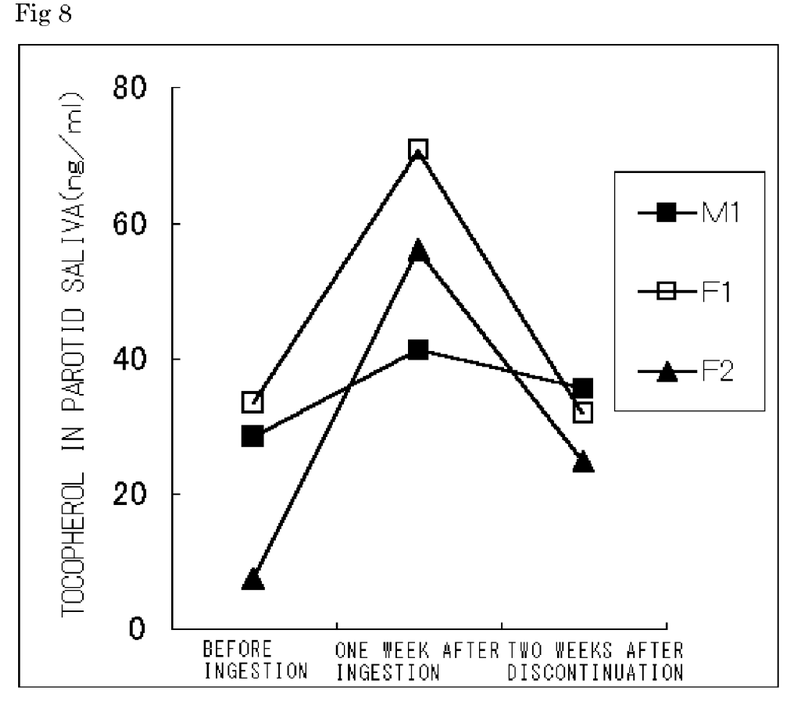
FIG. 8 shows transition of the tocopherol levels in parotid saliva before ingestion, during ingestion and at discontinuation of ingestion of a tocopherol-containing supplement.

Transition of the Tocopherol Concentration in Parotid Saliva Before and During Ingestion and at the Time of Discontinuation of Ingestion of the Supplement with Tocopherol 3 volunteers were made to ingest orally two commercial CoQ10 supplement S containing 32.8 mg of tocopherol per two tablets as α-tocopherol at 7:00 every morning continuously for a week, and as a specimen, parotid saliva was collected from PM 4:00 to 5:00, three times, that is, before ingestion and one week after ingestion and two weeks after discontinuation of ingestion. The volunteer had the mouth rinsed with water, and kept quiet on a chair for 5 minutes, while the volunteer accumulated saliva in the oral cavity and discharged to initialize the oral cavity, followed by collecting saliva. For collection of parotid saliva, the Saliva-sampler was inserted between the teeth and the cheek near the open of the parotid gland, the volunteer was made to sit quiet on a chair, during which saliva was collected, while the volunteer swallowed the sublingual gland and the submandibular gland to prevent contamination with saliva from the sublingual gland and the submandibular gland. In analysis of tocopherol in saliva collected from the parotid gland, the Saliva-sampler with absorbed saliva was transferred to the empty peculiar tube, to which 4 ml of isopropanol was added to have a final concentration of 80%. The resultant solution was mixed by flipping upside down for 10 minutes to extract from the absorber and coagulate proteins, and then centrifuged at 4° C. by 1000 G for removing fragments of the absorber and unnecessary proteins to get a supernatant, 20 µl of which was subjected to HPLC. The ingestion states of the supplement, that is, before ingestion and one week after ingestion, and two weeks after discontinuation of ingestion are arranged on the horizontal axis as points, and the tocopherol concentrations (hereinafter, the measured concentration of tocopherol will be referred to "tocopherol level") in parotid saliva are arranged on the vertical axis, and transition of the tocopherol level in parotid saliva depending on states of supplements with tocopherol is shown in FIG. 8. The tocopherol levels in parotid saliva were found to be increased by ingestion and decreased by discontinuation of ingestion, in reflection of ingestion states.

Example 8

Figure 9:
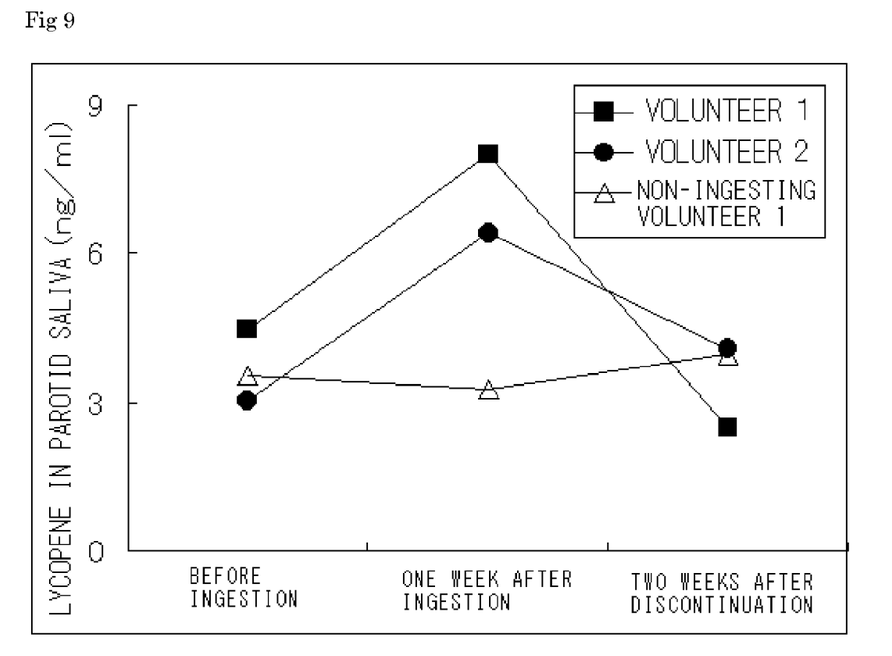
FIG. 9 shows transition of the lycopene levels in parotid saliva before ingestion, during ingestion and at discontinuation of ingestion of a lycopene and β-carotene-containing vegetable juice.
Figure 10:
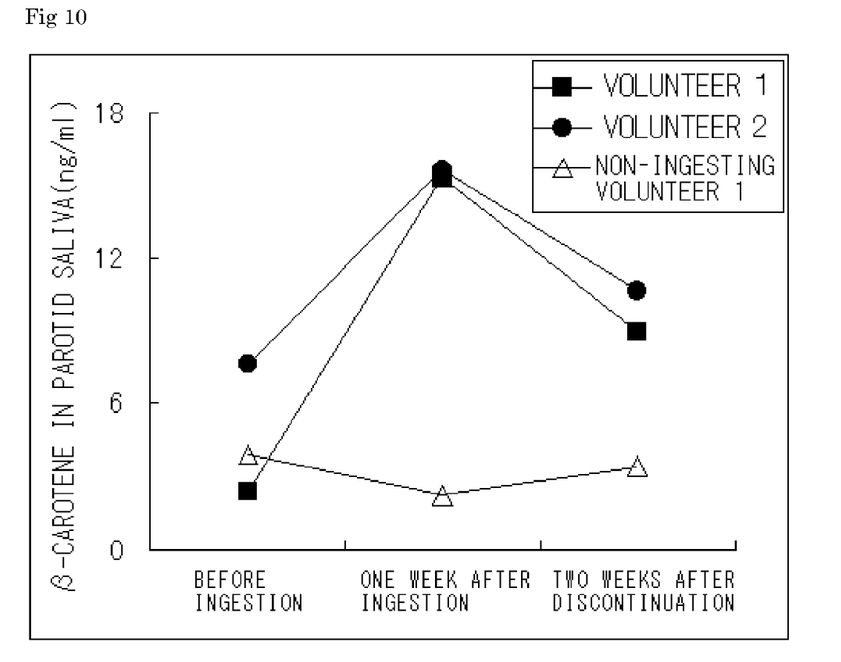
FIG. 10 shows transition of the β-carotene levels in parotid saliva before ingestion, during ingestion and at discontinuation of ingestion of a lycopene and β-carotene-containing vegetable juice.

Transition of the Lycopene and β-Carotene Concentrations in Parotid Saliva Before, During and at the Time of Discontinuation of Ingestion of the Commercial Supplement with Lycopene and β-Carotene 2 of 3 volunteers were made to ingest orally two commercial supplement lycopene +β-carotene MAX1 (trade name, Minami Healthy Food Co.) containing 10 mg of lycopene and 30 mg of β-carotene per one tablet (20 mg of lycopene and 60 mg of β-carotene per two tablet) at 7:00 every morning continuously for a week, and as a specimen, parotid saliva was collected from PM 4:00 to 5:00, three times, that is, before ingestion and one week after ingestion and two weeks after discontinuation of ingestion. The volunteer had the mouth rinsed with water, and kept quiet on a chair for 5 minutes, while the volunteer accumulated saliva in the oral cavity and discharged to initialize the oral cavity, followed by collecting saliva. For collection of parotid saliva, the Saliva-sampler was inserted between the teeth and the cheek near the open of the parotid gland, the volunteer was made to sit quiet on a chair, during which saliva was collected, while the volunteer swallowed the sublingual gland and the submandibular gland to prevent contamination with saliva from the sublingual gland and the submandibular gland. For analysis of lycopene and β-carotene in saliva collected from the parotid gland, the Saliva-sampler with absorbed saliva was transferred to the empty peculiar tube, to which 4 ml of isopropanol was added to have a final concentration of 80%. The resultant solution was mixed by flipping upside down for 10 minutes to extract from the absorber and coagulate proteins, and then centrifuged at 4° C. by 1000 G for removing fragments of the absorber and unnecessary proteins to get a supernatant, 150 µl of which was subjected to HPLC. The ingestion states of the supplement, that is, before ingestion and one week after ingestion, and two weeks after discontinuation of ingestion, are arranged on the horizontal axis as points, and the concentrations of lycopene and β-carotene (hereinafter, the measured concentrations of lycopene and β-carotene will be referred to "lycopene level" and "β-carotene level" respectively) in parotid saliva are arranged on the vertical axis, and transition of the lycopene and β-carotene levels in parotid saliva depending on ingestion of supplements is shown in FIGS. 9 and 10. The lycopene and β-carotene levels in parotid saliva were found to be obviously increased in the two volunteers who ingested the supplement compared with one volunteer without ingestion, and decreased by discontinuation of ingestion, in reflection of ingestion states.

Example 9

The Absorbent Materials for Parotid Saliva and Necessity of Extraction

In the method of preparing the specimens in example 2, the absorbent materials for saliva were weighed. 50 mg of an absorbent was soaked in 600 µl of saliva, 20 µl of saliva was fractionated to analyze the CoQ10 concentration in saliva transuaded from the absorbent, to which 180 µl of isopropanol was added, mixed, and centrifuged at 4° C. by 1000 G for 5 minutes to remove proteins, and 20 µl of the supernatant was subjected to HPLC. The results of analysis for CoQ10 are shown in Table 1 as "CoQ10 concentrations in saliva which was obtained by steps that 50 mg of the absorbent was soaked in 600 µl of saliva and the saliva was preserved in the interspace of the absorbent". It took about 3 minutes to secrete 1 ml of parotid saliva for the volunteers who spent little time, and 10 minutes or longer for the volunteers who spent lots of time, therefore it is practically difficult to collect without the absorbent. In this case, the fat-soluble food factors and the fat-soluble vitamins are adsorbed by any absorbent materials for saliva such as polyester, cotton and acetylcellulose. Although it is lowly absorptive, polyurethane fills water in saliva as bound water, so that condensation is caused, resulting in apparently high level (Refer to Table 1). Consequently, the adsorbed component should be extracted. For example, a cotton absorbent having contact with 2 ml of saliva which contains 1 ml of saliva in the interspace, substantially adsorbs components contained in 2 ml of saliva, demonstrating that results of higher level can be obtained by extraction compared with the case of contact with 1 ml of saliva. That means, a certain amount of saliva should be absorbed to a certain amount of absorbent in the oral cavity. Consequently, as for collection of saliva, a material which the saliva fraction once absorbed into an absorbent such as the Saliva-sampler by capillary phenomenon does not leak from the absorbent, and a collecting tool which color change of an indicator or the like informs a correct collection amount when absorbing a certain amount of saliva, should be used.

TABLE 1

| Treatment condition | CoQ10 (ng/ml) | Collection rate (%) |
|---|---|---|
| Saliva (control) | 33.7 | 100 |
| Cotton | 3.4 | 10.2 |
| Polyester | 19.6 | 58.2 |
| Polyurethane | 59.8 | 178 |
| Acetylcellulose | 25 | 7.3 |

Example 10

Confirmation of Extraction Effects Depending on Deproteinization Solvents

In the method of preparing the specimens in examples 1 and 2, the solvents were weighed using ethanol (90, 75, 50%), isopropanol (90, 75, 50%) or methanol (90, 75, 50%). Saliva of 600 µl, and 600, 1800 and 5400 µl of the solvent respectively were added to 50 mg of an absorbent to have a final concentrations of 50, 75 and 90% (V/V) respectively. The resultant solution was mixed, stirred, and centrifuged at 4° C. by 1000 G to get a supernatant, 20 μl of which was used to analyze CoQ10 by HPLC. As a result, the values shown in the following Table 2 "The CoQ10 concentrations in the supernatant obtained by deproteinizing saliva in three solvents and at three concentration levels (ng/ml)" were obtained. Ethanol, which was not affected by adsorption to proteins even at a concentration of 75% and could efficiently extract, was confirmed to be most suitable.

TABLE 2

| Concentration of the solvents used for deproteinization | Collection amount of CoQ10 by the solvents (ng/ml) | | |
|---|---|---|---|
| (V/V %) | isopropanol | ethanol | methanol |
| 90 | 56 | 98 | 61 |
| 75 | 19 | 86 | 2 |
| 50 | 23 | 3 | 2 |

Example 11

Confirmation of Extraction of Analysis Target Component Independent from the Absorbent Materials for Saliva In the method of preparing the specimens in example 2, the absorbent materials for saliva and the collection rate by extraction with 75% (V/V) ethanol were weighed. An absorbent of 50 mg was soaked in 600 μl of saliva, to which 180 μl of ethanol was added, mixed, and centrifuged at 4° C. by 1000 G or 5 minutes to remove proteins, and 20 μl of the supernatant was subjected to HPLC. The results of analysis for CoQ10 are shown in Table 3 as "CoQ10 concentrations in saliva which was obtained by steps that 50 mg of the absorbent was soaked in 600 μl of saliva and the saliva was extracted with 1800 μl of ethanol (final concentration: 75%)". It was found that the CoQ10 concentration in saliva extracted at 75% (V/V) did not depend on the absorbent materials for saliva, and approximately 100% collection could be achieved at 75% (V/V). Thus, although the fat-soluble components in saliva are adsorbed to the absorbent, the content in a certain amount of saliva can be determined by analyzing the summation of the fat-soluble food factors and the fat-soluble vitamins contained in saliva preserved in the absorbent and interspace.

TABLE 3

| Treatment condition | CoQ10 (ng/ml) | Collection rate (%) |
|---|---|---|
| Saliva (control) | 33.7 | 100 |
| Cotton + ethanol | 32.2 | 95.6 |
| Polyester + ethanol | 34.2 | 102 |
| Polyurethane + ethanol | 32.1 | 95.2 |
| Acetylcellulose + ethanol | 31.8 | 94.3 |

Example 12

Figure 11:
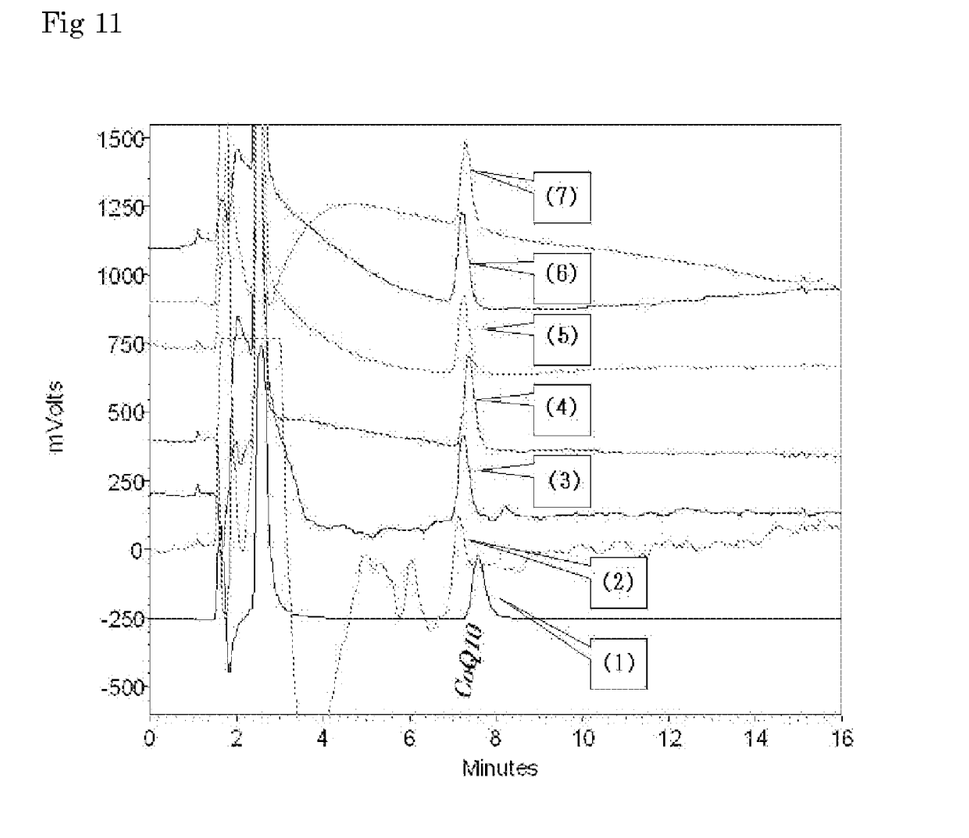
FIG. 11 shows chromatograms of CoQ10 standard solutions, indicating improvement effect of organic acids added to a mobile phase prepared using a substandard perchlorate.

Improvement Effects of Organic Acids Added to a Mobile Phase Prepared Using a Substandard Perchlorate on Chromatograms of CoQ10 Standard Solutions An example of good chromatogram form obtained by injecting 150 μl of a 50 ng/ml CoQ10 standard solution is shown in FIG. 11 (1), and an example of bad chromatogram form obtained by using perchlorate of substandard lot for preparing the mobile phase is shown in FIG. 11 (2). The good chromatogram form in FIG. 11 (1) can be obtained by using a sodium perchlorate (Lot No. 09704 KB, Sigma-Aldrichi Co.) or the like for preparing the mobile phase. The bad chromatogram form in FIG. 11 (2) was obtained by using sodium perchlorate (Lot No. 17129CA, KANTO CHEMICAL CO., INC.) for preparing the mobile phase. The good chromatogram form in FIG. 11 (3) was obtained by adding 5 mM sodium formate to the mobile phase which causes the bad chromatogram form in FIG. 11 (2) and by injecting 150 μl of a 50 ng/ml CoQ10 standard solution. Similarly, the good chromatogram forms in FIG. 11 (4), (5), (6) and (7) can be obtained by adding sodium acetate, glycine, sodium citrate, disodium EDTA (ethylenediamine tetraacetic acid) of 5 mM respectively to the mobile phase which causes the bad chromatogram form in FIG. 11 (2) and by injecting 150 μl of a 50 ng/ml CoQ10 standard solution. Improvement effects on a bad chromatogram form due to difference among manufacturers and lots of sodium perchlorate can be obtained by adding an organic acid to the mobile phase 2, more preferably to both mobile phases 1 and 2. The amount of the organic acid added to mobile phases 1 and 2 is 0.1-10 mM, preferably 3-7 mM, more preferably 5 mM, allowing measurement with no problem from the low-concentration side to the high-concentration side in the calibration curve. EDTA and citric acid of 5 mM may be insufficiently dissolved and deposited when added in the mobile phase, however even in such a case, improvement effects on the bad chromatogram form due to difference among manufacturers and lots of sodium perchlorate can be obtained.

The invention claimed is:

1. A method for inspecting in vivo migration of fat-soluble vitamins and/or fat-soluble food factors in a body of a subject, comprising analyzing fat-soluble vitamins and/or fat-soluble food factors in parotid saliva collected from the subject, wherein the fat-soluble vitamins and/or fat-soluble food factors are positively detected in the parotid saliva.

2. The method according to claim 1, wherein the parotid saliva is collected using a saliva collecting tool which collects parotid saliva selectively and quantitatively.

3. The method according to claim 2, wherein the saliva collecting tool has (a) a collection part comprising an absorber for absorbing saliva irreversibly and (b) a quantification part for quantifying the amount of saliva collected to the absorber.

4. The method according to claim 3, wherein the saliva collecting tool has further a storage container part for holding a saliva preservative solution in which the absorber with the absorbed saliva is dipped to preserve.

5. The method according to claim 4, wherein the saliva preservative solution is a water-soluble organic solvent.

6. The method according to claim 5, comprising:
(a) extracting the collected parotid saliva from the absorber with the absorbed parotid saliva, and/or from the preservative solution containing the absorber with absorbed parotid saliva using a water-soluble organic solvent, a hydrocarbon base organic solvent, or a mixture of isopropanol and ethyl acetate,
(b) separating the fat-soluble vitamins and/or the fat-soluble food factors from the extract by high-performance liquid chromatography, and
(c) detecting the separated fat-soluble vitamins and/or the fat-soluble food factors.

7. The method according to claim 1, comprising:
(a) extracting collected parotid saliva from an absorber with absorbed parotid saliva, and/or from a preservative solution containing an absorber with absorbed parotid saliva using a water-soluble organic solvent, a hydrocarbon base organic solvent, or a mixture of isopropanol and ethyl acetate,
(b) separating the fat-soluble vitamins and/or the fat-soluble food factors from the extract by high-performance liquid chromatography, and
(c) detecting the separated fat-soluble vitamins and/or the fat-soluble food factors.

8. The method according to claim 7, wherein the fat-soluble vitamins and/or the fat-soluble food factors are at least one substance selected from the group consisting of CoQ10, lycopene, β-carotene and tocopherol.

9. The method according to claim 1, wherein the fat-soluble vitamins and/or the fat-soluble food factors are at least one substance selected from the group consisting of CoQ10, lycopene, β-carotene and tocopherol.

10. A method for screening drugs, health supplements or foods, comprising carrying out the method according to claim 9, and determining whether to ingest the health supplements, drugs or foods comprising fat-soluble vitamins and/or fat-soluble food factors based on the results.

11. A method for screening drugs, health supplements, or foods comprising carrying out the method according to claim 1, and determining whether to ingest the health supplements, drugs or foods comprising fat-soluble vitamins and/or fat-soluble food factors based on the results.

12. A method for inspecting in vivo migration of fat-soluble vitamins and/or fat-soluble food factors contained in ingested health supplements, drugs or foods into a body of a subject, comprising analyzing fat-soluble vitamins and/or fat-soluble food factors in parotid saliva collected from the subject, wherein the fat-soluble vitamins and/or fat-soluble food factors are positively detected in the parotid saliva.

13. The method according to claim 12, wherein the inspecting is conducted by comparing the concentrations of the fat-soluble vitamins and/or fat-soluble food factors in the parotid saliva of the subject after ingestion of the health supplements, drugs or foods with either the concentrations of the fat-soluble vitamins and/or the fat-soluble food factors in the parotid saliva of the subjects before ingestion of the health supplements, drugs or foods, or with the mean concentrations of the fat-soluble vitamins and/or the fat-soluble food factors in the parotid saliva of a control group ingesting no health supplements, drugs or foods.

14. A method for assessing suitability of ingestion or intake of health supplements, drugs or foods comprising fat-soluble vitamins and/or fat-soluble food factors, comprising carrying out the method according to claim 13, and determining whether to ingest the health supplements, drugs or foods comprising fat-soluble vitamins and/or fat-soluble food factors based on the results.

15. A method for assessing suitability of ingestion or intake of health supplements, drugs or foods comprising fat-soluble vitamins and/or fat-soluble food factors comprising carrying out the method according to claim 12, and determining whether to ingest the health supplements, drugs or foods comprising fat-soluble vitamins and/or fat-soluble food factors based on the results.

16. A method for inspecting effect or action of an administered therapeutic agent on in vivo biosynthesis and metabolism of fat-soluble vitamins and/or fat-soluble food factors in a subject, comprising
analyzing fat-soluble vitamins and/or fat-soluble food factors in parotid saliva collected from the subject as indicators, wherein the fat-soluble vitamins and/or fat-soluble food factors are positively detected in the parotid saliva, and wherein an increase or decrease in the amount of the vitamins or food factors in the parotid saliva of the subject after being administered with a therapeutic agent compared with either the concentrations of the fat-soluble vitamins and/or the fat-soluble food factors in the parotid saliva of the subject before taking the therapeutic agent, or compared with the mean concentrations of the fat-soluble vitamins and/or the fat-soluble food factors in parotid saliva of a control group not having taken the therapeutic agent determines the effect of the therapeutic agent on the in vivo biosynthesis and metabolism of the vitamins and/or food factors in the subject.

17. A method for assessing suitability for administering or dosing a therapeutic agent having effect or action on biosynthesis and metabolism of fat-soluble vitamins and/or the fat-soluble food factors comprising carrying out the method according to claim 16, and determining whether to ingest the therapeutic agent based on the results.

18. A method for assaying for the presence of fat-soluble vitamins and/or fat-soluble food factors in a body of a subject, comprising analyzing fat-soluble vitamins and/or fat-soluble food factors in parotid saliva collected from the subject, and positively detecting the fat-soluble vitamins and/or fat-soluble food factors.

19. The method according to claim 18, wherein the fat-soluble vitamins and/or the fat-soluble food factors are at least one substance selected from the group consisting of CoQ10, lycopene, β-carotene and tocopherol.

20. The method according to claim 18, wherein the parotid saliva is collected using a saliva collecting tool which collects parotid saliva selectively and quantitatively.

21. The method according to claim 18, comprising:
(a) extracting collected parotid saliva from an absorber with absorbed parotid saliva, and/or from a preservative solution containing an absorber with absorbed parotid saliva using a water-soluble organic solvent, a hydrocarbon base organic solvent, or a mixture of isopropanol and ethyl acetate,
(b) separating the fat-soluble vitamins and/or the fat-soluble food factors from the extract by high-performance liquid chromatography, and
(c) detecting the separated fat-soluble vitamins and/or the fat-soluble food factors.

* * * * *